United States Patent
Ruhs et al.

(10) Patent No.: US 8,461,998 B2
(45) Date of Patent: Jun. 11, 2013

(54) DEVICE TO BE WORN ON THE HUMAN OR ANIMAL BODY FOR DETECTING BODY-RELATED DATA AND METHOD FOR ACTIVATING OR DEACTIVATING SUCH A DEVICE

(75) Inventors: Mirko Ruhs, Heppenheim (DE); Thorsten Sohnke, Asperg (DE)

(73) Assignee: Robert Bosch GmbH, Stuttgart (DE)

( * ) Notice: Subject to any disclaimer, the term of this patent is extended or adjusted under 35 U.S.C. 154(b) by 522 days.

(21) Appl. No.: 12/771,776

(22) Filed: Apr. 30, 2010

(65) Prior Publication Data

US 2010/0283616 A1 Nov. 11, 2010

(30) Foreign Application Priority Data

May 7, 2009 (DE) .......................... 10 2009 002 906

(51) Int. Cl.
*G08B 23/00* (2006.01)

(52) U.S. Cl.
USPC ........................................ 340/573.1; 340/3.1

(58) Field of Classification Search
USPC ..................... 340/573.1, 573.4, 3.1
See application file for complete search history.

(56) References Cited

U.S. PATENT DOCUMENTS

| | | | | |
|---|---|---|---|---|
| 5,543,780 | A  * | 8/1996 | McAuley et al. | 340/572.1 |
| 5,982,285 | A  * | 11/1999 | Bueche et al. | 340/573.1 |
| 6,169,494 | B1 * | 1/2001 | Lopes | 340/8.1 |
| 6,426,719 | B1 * | 7/2002 | Nagareda et al. | 342/357.52 |
| 6,608,562 | B1 * | 8/2003 | Kimura et al. | 340/573.1 |
| 6,923,571 | B2 * | 8/2005 | Ellenz | 374/45 |
| 7,127,370 | B2 * | 10/2006 | Kelly et al. | 702/151 |
| 7,742,995 | B2 * | 6/2010 | Phillips | 705/65 |
| 8,212,650 | B2 * | 7/2012 | Tsern et al. | 340/3.1 |
| 2008/0117060 | A1 * | 5/2008 | Cuddihy et al. | 340/573.1 |

* cited by examiner

*Primary Examiner* — Jennifer Mehmood
*Assistant Examiner* — Andrew Bee
(74) *Attorney, Agent, or Firm* — Kenyon & Kenyon LLP

(57) ABSTRACT

A device to be worn on the human or animal body for detecting body-related data using a detection element for detecting a temperature in or on the device and an element for activating and deactivating the device by taking the detected temperature into account.

11 Claims, 1 Drawing Sheet

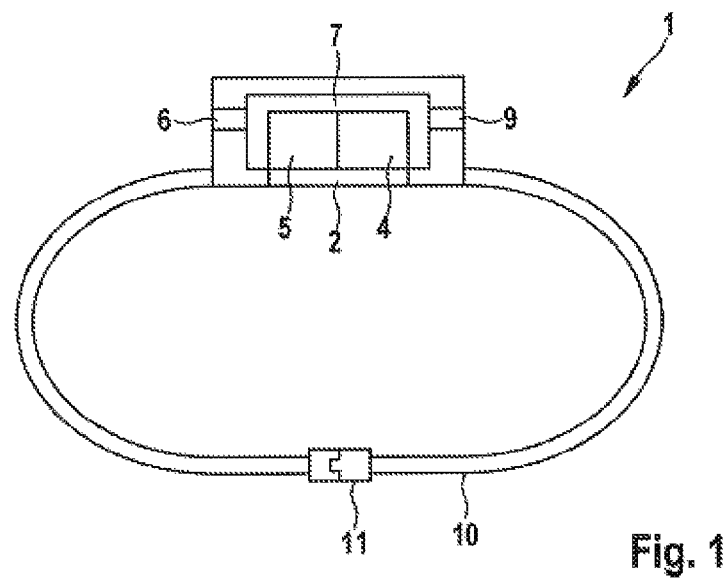
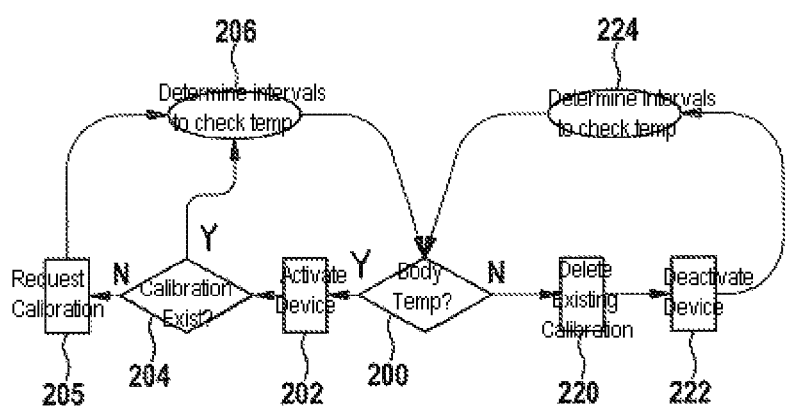

DEVICE TO BE WORN ON THE HUMAN OR ANIMAL BODY FOR DETECTING BODY-RELATED DATA AND METHOD FOR ACTIVATING OR DEACTIVATING SUCH A DEVICE

BACKGROUND INFORMATION

Devices to be worn on the body for detecting body-related data are known. Sensors for detecting movements are mentioned as an example. Various manufacturers of sports equipment for example sell pedometers and speedometers for sports activities. From the medical field, sensors are also known that detect e.g. movements and/or pulse data and/or additional data.

Furthermore, sensors are known which infer physiological values, for example stress or body temperature load, from detecting a body temperature.

Such devices must be switched on manually prior to use. Furthermore, they should be expediently switched off following their use so as to minimize battery or power consumption for example. After putting them on, it is often necessary to calibrate such devices, for which purpose the user must normally push a button or a key. Such a calibration is necessary in order to determine the attachment position (angle) on the body for example. A calibration is expediently performed in a state of rest, for example by determining the direction of gravitation.

A main target group of the mentioned devices for detecting physiological values are sick or old people, who normally are technologically not very versed or interested. In particular, a person may inadvertently fail to activate or deactivate the device, which may result in a false or erroneous classification of detected data. In particular in the case of a medical device, an interaction with the user proves to be a frequent cause of error. In this connection, reference should be made in particular to activation (switching on), deactivation (switching off) and calibration. For this reason it is desirable to operate such devices reliably without or with as few user inputs as possible.

SUMMARY OF THE INVENTION

According to the present invention, a manual activation or deactivation of a device to be worn on the body for detecting body-related data is no longer necessary. The present invention creates a very reliable (and at the same time inexpensively implementable) possibility for ensuring such an activation and deactivation independently of a concrete activity/action of the user. Since no manual activation or deactivation is required, the present invention is also suitable for use on animals.

According to a preferred specific embodiment, the detection element is developed to compare the detected temperature to a reference temperature, the activation or deactivation occurring by taking into account a performed comparison of the detected temperature with the reference temperature. The activation or deactivation may occur for example as a function of whether the detected temperature is above or below the reference temperature.

Such a comparison of a detected temperature to a reference temperature may be carried out in particularly simple fashion electronically and/or by calculation, whereby an activation or deactivation of the device is ensured reliably.

Expediently, a temperature in the range of a body temperature is used as the reference temperature, that is, in particular in the range between 36 and 42° C.

The device according to the present invention is typically fastened on the skin, for example on the foot, leg, arm or chest by a rubber band or an elastic lock. If the device is worn directly on the body, the fact that it is worn may be detected via a comparison of the detected temperature and the body temperature. If the device for example has no temperature in the range of the body temperature, then it may be assumed that the device has not been put on and is not in use. Normally the ambient temperature will be below the body temperature. In this case, the device is deactivated for example if the detected temperature falls below a typical value for a body temperature, for example 36 or 37° C. When using the device according to the present invention in surroundings, in which the temperature is higher than a typical body temperature, for example in tropical countries, a corresponding deactivation may also be set for the event that the detected temperature is above a typical body temperature. For example, the device could be deactivated at a detected temperature of 43 or 44° C.

Such a deactivation in particular helps to prevent a misclassification of data. The device may classify this time period as "unknown" since the user is not using the device in the time period in which respective temperatures deviating from the body temperature are detected. For example, the following traditionally occurring erroneous classifications may be avoided effectively:

In conventional devices, the situation may occur that the user takes off the device, but does not switch it off. In this case, for example if the device is developed as a motion sensor, a "patient lying down" is detected even though the user is possibly still moving.

On the other hand, in conventional devices, the sensor may be put on without being activated. In this situation, the device would detect no data even though the user wears the sensor on his body and there would be relevant data to be detected.

Furthermore, reference may be made to the situation in which the device is located for example in a backpack, in a bag, or also for example in the trunk of a car, and is moved. If the device is not deactivated in this case, such a movement could result in misclassifications.

All false detections or misclassifications of this kind may be avoided using the design approach according to the present invention because the device is automatically activated or deactivated, merely as a function of a detected temperature or a comparison of the detected temperature to a reference temperature, in particular a body temperature.

As an additional refinement, the detection of temperature transitions or temperature changes should be mentioned. For example, the fact that a device is put on or taken off may be recognized by detecting a temperature change from an ambient temperature, which is different from the body temperature, toward the body temperature. A removal of the sensor from the body may be detected in a corresponding manner.

The device is expediently developed as a motion sensor. Phases of activity and phases of rest of a user may be detected effectively and reliably by the measure according to the present invention of activating or deactivating such a motion sensor automatically by way of temperature detection.

In the course of putting on or taking off a device, a calibration may also be performed in a simple and reliable manner.

Such a motion sensor expediently has means for performing a calibration following an activation. It proves to be practical in particular to perform such a calibration only when the user is sufficiently still when putting on or after putting on the device, e.g. when standing still or sifting. In the event that the user does not stand still when putting on the device, it is possible to wait for a sufficiently still phase so as then to perform a calibration. Until such a calibration is performed, it is possible to calculate using "standard values". In particular, a "flag" may be set to indicate that the sensor is now being worn and should be calibrated.

When the sensor is taken off and there is an associated detection of a lower temperature in accordance with the present invention, then the calibration is no longer valid or may be declared to be invalid. A calibration may thus be expediently deleted immediately after the sensor is taken off in order to prevent possibly the use of unsuitable values after the sensor is put on again.

According to another specific embodiment, it proves to be advantageous to detect the temperature of the surroundings as well. With this additional information, a device developed according to the present invention may be put on or removed in an even more reliable fashion. Using an additionally detected ambient temperature, it is also possible to estimate an expected value of the body temperature such that the reference temperature used as the body temperature may possibly be adapted to a concrete ambient temperature. In this way it is possible to ensure a reliable operation for example at an ambient temperature in the range of typical body temperatures.

Furthermore, the detection element expediently has means for detecting additional data, which make it possible to infer that the device is worn on a body. In this connection, one should think of pulse detection means, skin conductivity detection means or skin humidity detection means for example.

The detection of such data in addition to the temperature detection according to the present invention ensures an even greater certainty and reliability in a desired activation or deactivation of the device.

BRIEF DESCRIPTION OF THE DRAWINGS

FIG. 1 shows a schematic lateral view of a preferred specific embodiment of the device according to the present invention.

FIG. 2 shows a flow chart in particular for representing a preferred specific embodiment of the method according to the present invention.

DETAILED DESCRIPTION

FIG. 1 shows a preferred specific embodiment of the device according to the present invention, which is to be worn on the arm of a user, indicated as a whole by 1. Respective devices may also be developed so as to be worn on a foot or on the chest or at another desired location on the body.

Device 1 may be developed as a motion sensor for example. It may be fastened on the arm with the aid of an armband 10, which is developed with a locking device 11 for example.

Device 1 has a detection element 2 developed for example as a temperature sensor for detecting the temperature of the arm and thus the body temperature of a user. Expediently, detection element 2 is provided on the inner side of device 1, i.e. directly adjacent to the arm of the user.

The temperature or body temperature detected by detection element 2 is provided on an element 4 for activating and/or deactivating the device, which is likewise provided in device 1. This element 4 activates device 1 as a function of whether the temperature detected by detection element 2 corresponds to a body temperature. Advantageously, device 1 is calibrated by a calibration element 5 as a function of the detected temperature and a resulting activation. Elements 4 and 5 are advantageously developed as components of a computing element 7.

According to an advantageous refinement of the present invention, device 1 has another element 6 for detecting an ambient temperature, which is likewise connected to elements 4 or 5 or the computing element. Furthermore, means 9 may be provided for detecting additional data, which allow for the inference that the device is worn on a body.

A preferred specific embodiment of the method according to the present invention will now be explained with reference to FIG. 2.

In a step 200, first a determination is made (by detection element 2) as to whether a detected temperature corresponds to a body temperature or not. If this is the case, device 1, for example a motion sensor, is activated in a step 202. Following the activation of the sensor, computing element 7 determines whether the device is calibrated or not (step 204). If this is the case, a determination is made in a step 204 that an on-state obtains, i.e. that the device is worn on the body of a user. If it is determined in step 204 that no calibration exists, then a calibration is requested and performed in a step 205. Subsequently, the method proceeds to the mentioned step 206.

If a determination is made in step 200, however, that a detected temperature does not correspond to a body temperature, then first in a step 220 a possibly existing calibration of the system is deleted in order to avoid misinterpretations of data. Subsequently, in a step 222, device 1 or the motion sensor in the example shown is deactivated. In a subsequent step 224, a determination is made that the device is in an off-state, i.e. that it is currently not worn by a user. Starting from steps 206 or 224, step 200 may be performed either at regular intervals or in the event of an ascertained temperature change.

What is claimed is:

1. A device to be worn on a human or animal body for detecting physiological body-related data, comprising:
   at least one sensor adapted for detecting a temperature in or on the device and an ambient temperature; and
   a computing component adapted for:
      generating an expected value of a body temperature based on the ambient temperature;
      comparing the temperature detected in or on the device to a reference temperature that is based on, and in a range of, the expected value of the body temperature; and
      activating and deactivating the device based on a result of the comparison.

2. The device according to claim 1, wherein the at least one sensor detects temperature changes or temperature transitions.

3. The device according to claim 1, wherein the device is a motion sensor.

4. The device according to claim 1, wherein the computing component is adapted for performing a calibration following an activation.

5. The device according to claim 1, further comprising a sensor for detecting additional data representing at least one of a pulse, skin conductivity, and skin humidity, which allow for an inference that the device is put on a body.

6. A method for activating or deactivating a device to be worn on a body for detecting physiological body-related data, the method comprising:
   detecting a temperature in or on the device;
   detecting an ambient temperature;
   generating an expected value of a body temperature based on the ambient temperature;

comparing the temperature detected in or on the device to a reference temperature, the reference temperature being based on, and in a range of, the expected value of the body temperature; and activating or deactivating the device based on a result of the comparison.

7. A device to be worn on a human or animal body for detecting body-related data, comprising:
- at least one sensor adapted for detecting a temperature in or on the device and an ambient temperature; and
- a computing component adapted for:
  - generating an expected value of a body temperature based on the ambient temperature;
  - comparing the detected temperature in or on the device to a reference temperature that is based on, and in the range of, the expected value of the body temperature; and
  - activating and deactivating the device based on a result of the comparison.

8. The device according to claim 7, wherein the computing component is programmed to select the reference temperature from a programmatically specified temperature range of 36-42° C.

9. The device according to claim 8, wherein the body-related data is physiological body-related data.

10. The device according to claim 7, wherein the computing component is programmed to select the reference temperature from a programmatically specified temperature range of 36-44° C.

11. The device according to claim 10, wherein the body-related data is physiological body-related data.

* * * * *